(12) United States Patent
Lorenz et al.

(10) Patent No.: US 10,226,352 B2
(45) Date of Patent: Mar. 12, 2019

(54) IMPLANT

(71) Applicant: Ulrich GmbH & Co. KG, Ulm (DE)

(72) Inventors: Julia Lorenz, Neu-Ulm (DE); Martin Schroeter, Weissenhorn (DE); Tobias Winkler, Dornstadt (DE); Harry Christenhusz, Bad Bentheim (DE); Hubertus Paul Maria Ter Braak, Haaksbergen (NL)

(73) Assignee: Ulrich GmbH & Co. KG, Ulm (DE)

( * ) Notice: Subject to any disclaimer, the term of this patent is extended or adjusted under 35 U.S.C. 154(b) by 212 days.

(21) Appl. No.: 15/259,628

(22) Filed: Sep. 8, 2016

(65) Prior Publication Data
US 2017/0065425 A1 Mar. 9, 2017

(30) Foreign Application Priority Data
Sep. 8, 2015 (EP) .................................... 15184164

(51) Int. Cl.
*A61F 2/44* (2006.01)
*A61F 2/30* (2006.01)

(52) U.S. Cl.
CPC .............. *A61F 2/44* (2013.01); *A61F 2/4455* (2013.01); *A61F 2002/30115* (2013.01); *A61F 2002/30131* (2013.01); *A61F 2002/30329* (2013.01); *A61F 2002/30471* (2013.01); *A61F 2002/30477* (2013.01); *A61F 2002/30495* (2013.01); *A61F 2002/30505* (2013.01); *A61F 2002/30528* (2013.01); *A61F 2002/30538* (2013.01); *A61F 2002/30777* (2013.01); *A61F 2002/30841* (2013.01)

(58) Field of Classification Search
CPC .......... A61F 2/44; A61F 2/4455; A61F 2/446; A61F 2/4465; A61F 2/447; A61F 2002/4475
USPC ............................................ 623/17.15, 17.16
See application file for complete search history.

(56) References Cited

U.S. PATENT DOCUMENTS

| 5,480,442 | A | 1/1996 | Bertagnoli |
| 6,808,538 | B2 * | 10/2004 | Paponneau ............... A61F 2/44 623/17.16 |

(Continued)

FOREIGN PATENT DOCUMENTS

| DE | 44 17 629 A1 | 1/1995 |
| RU | 96000 U1 | 7/2010 |

*Primary Examiner* — Eric S Gibson
(74) *Attorney, Agent, or Firm* — Muncy, Geissler, Olds & Lowe, P.C.

(57) ABSTRACT

An implant for insertion between vertebral bodies of the spinal column, with a main body which is formed along a longitudinal axis and at least one end of which an attachment plate with a contact surface for attachment to an adjacent vertebral body is disposed, which plate is mounted on main body pivotably about a pivot axis, arranged substantially perpendicular to the longitudinal axis, and which can be fixed at an angle relative to it or relative to the longitudinal axis. The main body is assigned at least one clamping element. The attachment plate has a clamping surface on a side facing the main body, and the clamping element is movable between a pivot configuration, in which the attachment plate is pivotable, and a clamping configuration, in which the angle and thereby the attachment plate are fixed by an interaction of the clamping element with the clamping surface.

20 Claims, 7 Drawing Sheets

(56) References Cited

U.S. PATENT DOCUMENTS

| | | | | |
|---|---|---|---|---|
| 8,034,111 B2* | 10/2011 | Hsu | A61F 2/44 | 623/17.11 |
| 8,157,864 B2* | 4/2012 | Rogeau | A61F 2/44 | 623/17.11 |
| 8,202,321 B2* | 6/2012 | Gerner | A61F 2/44 | 623/17.11 |
| 8,211,178 B2* | 7/2012 | Melkent | A61F 2/44 | 623/17.16 |
| 9,561,113 B2* | 2/2017 | Howard | A61F 2/442 | |
| 9,801,730 B2* | 10/2017 | Howard | A61F 2/442 | |
| 2003/0045877 A1* | 3/2003 | Yeh | A61F 2/44 | 606/247 |
| 2005/0004572 A1* | 1/2005 | Biedermann | A61F 2/44 | 623/17.15 |
| 2005/0060036 A1* | 3/2005 | Schultz | A61F 2/44 | 623/17.15 |
| 2006/0058879 A1* | 3/2006 | Metz-Stavenhagen | A61F 2/44 | 623/17.15 |
| 2006/0200244 A1* | 9/2006 | Assaker | A61F 2/44 | 623/17.15 |
| 2010/0324687 A1* | 12/2010 | Melkent | A61F 2/44 | 623/17.16 |
| 2011/0106258 A1* | 5/2011 | Blackwell | A61F 2/30734 | 623/17.16 |
| 2011/0184523 A1* | 7/2011 | Blackwell | A61F 2/44 | 623/17.16 |
| 2011/0190890 A1* | 8/2011 | Blackwell | A61F 2/44 | 623/17.16 |
| 2012/0016476 A1* | 1/2012 | Wilfong | A61F 2/44 | 623/17.11 |
| 2012/0016478 A1* | 1/2012 | Wilfong | A61F 2/44 | 623/17.16 |
| 2012/0029634 A1* | 2/2012 | Drochner | A61F 2/4455 | 623/17.11 |
| 2012/0029640 A1* | 2/2012 | Capote | A61F 2/44 | 623/17.16 |
| 2012/0109302 A1* | 5/2012 | Miller | A61F 2/44 | 623/17.11 |
| 2012/0109307 A1* | 5/2012 | Drochner | A61F 2/4455 | 623/17.16 |
| 2014/0277510 A1 | 9/2014 | Robinson et al. | | |
| 2016/0100955 A1* | 4/2016 | Stinchfield | A61F 2/4465 | 623/17.15 |
| 2016/0175105 A1* | 6/2016 | Howard | A61F 2/442 | 623/17.16 |
| 2017/0065425 A1* | 3/2017 | Schilling | A61F 2/44 | |

* cited by examiner

IMPLANT

This nonprovisional application claims priority under 35 U.S.C. § 119(a) to European Patent Application No. 15184164.0, which was filed in Europe on Sep. 8, 2015, and which is herein incorporated by reference.

BACKGROUND OF THE INVENTION

Field of the Invention

The invention relates to an implant for insertion between vertebral bodies of the spinal column, with a main body which is formed along a longitudinal axis and at the at least one end of which an attachment plate with a contact surface for attachment to an adjacent vertebral body is disposed, which plate is mounted on the main body pivotably about a pivot axis, arranged substantially perpendicular to the longitudinal axis, and which can be fixed at an angle relative to the main body or to the longitudinal axis.

Description of the Background Art

Implants of this kind are known, for example, from DE 44 17 629 A1, which corresponds to U.S. Pat. No. 5,480,442, which describes a spinal column implant with a main body, at both ends of which an attachment plate is disposed, which after the angular position is set relative to the main body can be rigidly connected to it. It is disadvantageous in this case that after the angle is set the fixation of the same occurs either by filling in of bone material or by introduction of a curable medium. This represents a complex procedure for the subsequent fixation of the set angle and moreover is also irreversible. A subsequent changing of the angle cannot be corrected after the fixation.

SUMMARY OF THE INVENTION

It is therefore an object of the present invention to provide an improved implant.

In an exemplary embodiment an implant is provided in that the main body is assigned at least one clamping element, the attachment plate has a clamping surface on a side facing the main body, and the clamping element is movable between a pivot configuration, in which the attachment plate is pivotable, and a clamping configuration, in which the angle and thereby the attachment plate are fixed by an interaction of the clamping element with the clamping surface. The angle of the attachment plate relative to the longitudinal axis can be fixed by a clamping connection in a very simple manner by the interaction between the clamping element and the clamping surface. The time-consuming fixation of the angle of the attachment plate by screws or by introduction of a fixative material is therefore eliminated. The pivotable mounting of the attachment plate relative to the main body in addition enables a stepless and therefore very fine and precise adjustment of the optimal angle. It is possible to fix the angle reversibly because the clamping element can be moved between a pivot configuration and a clamping configuration, in other words, to be able to correct at a later time or to optimize a previously set and fixed angle between the attachment plate and the longitudinal axis. This enables the surgeon to find and set the optimal angle in a rapid manner, so that the contact surface lies optimally at the vertebral body. This also prevents the caving of the vertebral body replacement into the adjacent vertebral body because of an optimal load distribution. Alternatively or in addition, it is advantageous if the angle can be fixed irreversibly, and the clamping element therefore, if it was moved to the final clamping configuration, can no longer be set back into the pivot configuration. Within the scope of the invention, it is advantageous furthermore that each end of the main body is assigned an attachment plate with a contact surface for attachment to the adjacent vertebral body, said plate which is mounted on the main body and in each case is pivotable about a pivot axis arranged substantially perpendicular to the longitudinal axis and can be fixed at an angle relative to the main body or relative to the longitudinal axis, that the main body is assigned at least one clamping element for each attachment plate, that the attachment plates have at least one clamping surface on a side facing the main body, and that the clamping elements are movable between a pivot configuration, in which the attachment plates are pivotable, and a clamping configuration, in which the angle and thereby the attachment plates are fixed by the interaction of the clamping elements with the clamping surfaces. This makes it possible that the implant can be fitted even more precisely to the form and orientation of the adjacent vertebral bodies.

In an embodiment, the attachment plate has a plurality of clamping surfaces on a side facing the main body. In this case, the clamping surfaces can be formed along the longitudinal axis of the attachment plate or, however, in a preferred embodiment, approximately perpendicular to the longitudinal axis. The main body in an advantageous embodiment has an edge on the side facing the attachment plate. It is used inter alia to limit the adjustable angle and is used as a stop for the clamping element. Furthermore, the main body is preferably formed as a hollow body and has one or more recesses circumferentially on the lateral surface of the main body.

In an embodiment, the clamping element is formed as a clamping swivel and each attachment plate is assigned two of the clamping swivels that are mounted pivotably on the main body. A clamping connection forms between the clamping swivels and the clamping surfaces of the attachment plate by swiveling the clamping swivels about a clamping axis within the framework of the clamping configuration.

In an embodiment, the clamping element can be formed as a sleeve, which is mounted on the main body and is movable opposite to the direction of the attachment plate. A clamping connection can again be formed between the clamping surface of the attachment plate and the sleeve by moving the sleeve along the longitudinal axis of the main body.

In an embodiment, the clamping element can be formed as a sliding element which can be moved in and opposite to the direction of the attachment plate on the main body along the longitudinal axis and in this way can make preferably reversibly a clamping connection with the clamping surface.

In an embodiment of the invention, it is provided further that the clamping element can be mounted on the main body pivotably about an axis arranged substantially perpendicular to the longitudinal axis. An especially rapid setting or fixation of the clamping configuration can occur by the pivotable mounting of the clamping element on the main body. In this case, it is provided in one embodiment that the clamping element and the attachment plate are mounted pivotably about the same pivot axis. Alternatively and in a preferred embodiment, the clamping element is pivotable about an axis which is oriented perpendicular to the longitudinal axis and is formed as a clamping axis, whereby the pivot axis and the clamping axis are preferably oriented substantially parallel to one another.

Furthermore, the clamping element can be formed as a clamping bracket which surrounds at least partially the main body circumferentially. The design of the clamping element as a clamping bracket forms an especially easy-to-manipulate clamping element, which can be moved in a simple manner between the clamping configuration and the pivot configuration. In one embodiment in which the clamping configuration is provided as irreversible, a predetermined breaking point is formed preferably on the clamping bracket in the material, for example, in form of an indentation, so that the clamping bracket can be broken off after the final fixation of the angle.

It is advantageous in particular if an extension, which comprises in particular an at least partially planar securing surface, is formed or disposed on the outer circumference of the main body. Said extension is used for the additional securing of the clamping element or of the clamping bracket in the clamping configuration. In this case, the clamping bracket when moving into the clamping configuration is pushed over the securing surface, as a result of which the securing surface and the clamping bracket preferably form a frictional connection. The securing surface in this case can also be formed as a securing line.

It is provided in this connection that the extension is inclined at a tilt angle or is oriented substantially parallel to the longitudinal axis. In the case of an extension inclined at a tilt angle, it is conceivable that the extension has a plateau on which the clamping element rests in the clamping configuration.

The clamping element can be assigned at least one coupling member on the side facing the clamping surface for additional securing of the clamping configuration. The coupling member in this case can be formed as a catch member with a catch seat formed on the clamping surface. It is particularly preferred, nevertheless, if the coupling member is formed as a single barb or as a plurality of barbs. It is especially advantageous in this case, if the barbs can cut into the clamping surface for the additional securing of the clamping configuration.

It is provided, furthermore, that the attachment plate and the main body can be connected to one another by a pivot unit, which comprises a projection, facing the main body, with a connecting member seat, a projection seat, formed on the main body, with a connecting member opening, and a connecting member inserted in the connecting member seat and in the connecting member opening. The pivot unit in this case represents a structurally especially simple solution for mounting the attachment plate pivotably on the main body. In this case, the pivoting movement of the attachment plate is guided by the pivoting movement of the projection in the projection seat. As a result, the angle can be set especially finely or precisely. It is advantageous in particular if the connecting member is formed as a bolt or pin. It is provided further that the connecting member opening is shaped as a long hole. In a further embodiment of the invention, the long hole enables a limited lateral movability of the connecting member in the long hole and thereby of the attachment plate relative to the main body. As a result, the pivoting angle of the attachment plate about the pivot axis is increased and the implant can be fitted even more optimally to the form and orientation of the adjacent vertebral bodies. It is preferred further if each attachment plate is connected by two pivot units to the main body and if the pivot units are arranged distributed uniformly over the circumference of the attachment plate or of the main body. It is provided alternatively that the connecting member opening shaped as a long hole is formed on the attachment plate, that a connecting member seat is disposed on the main body, and that a connecting member formed as a pin is taken up in the connecting member seat and the connecting member opening.

The projection can be formed at least partially convex and if the projection seat is preferably formed at least partially concave. As a result, the pivoting movement can be guided especially well, whereby it is provided in particular that the projection is formed as convex and the projection seat as concave matching the convex structure. In other words, the projection and the projection seat form a joint. This enables an especially precise setting of the angle and thereby also an especially simple fixation of the angle. It is beneficial in this context, if only parts of the convex projection are taken up in the concave projection seat. In an alternative embodiment, the projection seat can also be formed planar.

It is provided in an embodiment that the attachment plate and the main body can be connected to one another by a pivot unit, which comprises a pivot member and a pivot member seat formed on the main body. The pivot member in this case can be formed, for example, as a pin or bolt, which engages in the pivot member seat and is mounted pivotably therein.

The clamping element and the main body can be connected to one another by a pivot, which comprises a clamping element connecting member seat formed on the clamping element, a clamping element connecting member opening formed on the main body, and a clamping element connecting member inserted in the clamping element connecting member seat and in the clamping element connecting member opening. This makes it possible for the clamping element to be mounted pivotably on the main body. It is especially advantageous in this case if the clamping bracket connecting member is formed as a bolt or pin. It is provided further that each clamping element is assigned a pivot and that the pivot are arranged distributed uniformly over the circumference of the main body. A type of pivoting joint is also formed. If the clamping element is formed as a clamping bracket, then it is preferable, if the clamping bracket is connected by precisely two pivot to the main body. It is preferred further that the clamping element is made with a larger diameter in the area of the pivot. This enables a higher load-bearing capacity of the clamping element and prevents the breaking off of the clamping element when it is moved into the clamping configuration.

The main body at the end facing the pivoting unit can have a reinforcement in which the projection seat with the connecting member opening and the clamping bracket connecting member opening are formed. In this regard, the reinforcement extends at least partially circumferentially on the main body. The reinforcement improves the load-bearing capacity of the implant and prevents the attachment plate from breaking off from the main body during implantation and fixation.

The main body can have a clamping bracket seat for receiving a clamping bracket extension formed on the clamping bracket. The extension is used to secure the clamping bracket on the main body in the pivot configuration. It has proven useful furthermore, if a flexible element is disposed on the main body for securing the clamping element in the clamping configuration. Preferably, the flexible element is formed as a snap-in element with a radially outwardly projecting end. It is preferred further if the flexible element is pretensioned preferably radially in the pivot configuration.

The flexible element in the pivot configuration can act axially on the clamping bracket extension and that the clamping bracket extension in the clamping configuration acts radially together with the clamping bracket seat. In this case, the clamping bracket extension is provided along the longitudinal axis of the main body resting on the flexible element. This secures the clamping bracket in the pivot configuration. The radial interaction of the clamping bracket extension and the clamping bracket seat in the clamping configuration is used for the additional securing of the clamping configuration or the clamping connection.

An advantage of the present invention is that the implant can be manipulated very easily and therefore can be implanted intervertebrally in a relatively simple manner and can be oriented optimally in regard to the adjacent vertebral bodies. As a result, the implant can be inserted variably along the spinal column. An angle of the attachment plate relative to the main body can be established in a simple manner by the attachment plate mounted pivotably on the main body, so that the attachment plate is oriented optimally relative to the adjacent vertebral bodies. A frictional connection between the clamping element and clamping surface is formed or a clamping connection is formed by the interaction between the clamping element and the clamping surfaces disposed on the attachment plate. This clamping connection makes it possible to determine or to fix the previously selected angle securely and in a time-saving manner. The moving of the clamping element between the clamping configuration and the pivot configuration, and the setting of the angle in the pivot configuration requires no or only very few additional instruments. Consequently, the implant can be adapted especially easily and in a simple manner to the conditions in the spinal column of the human body.

Further scope of applicability of the present invention will become apparent from the detailed description given hereinafter. However, it should be understood that the detailed description and specific examples, while indicating preferred embodiments of the invention, are given by way of illustration only, since various changes, combinations and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
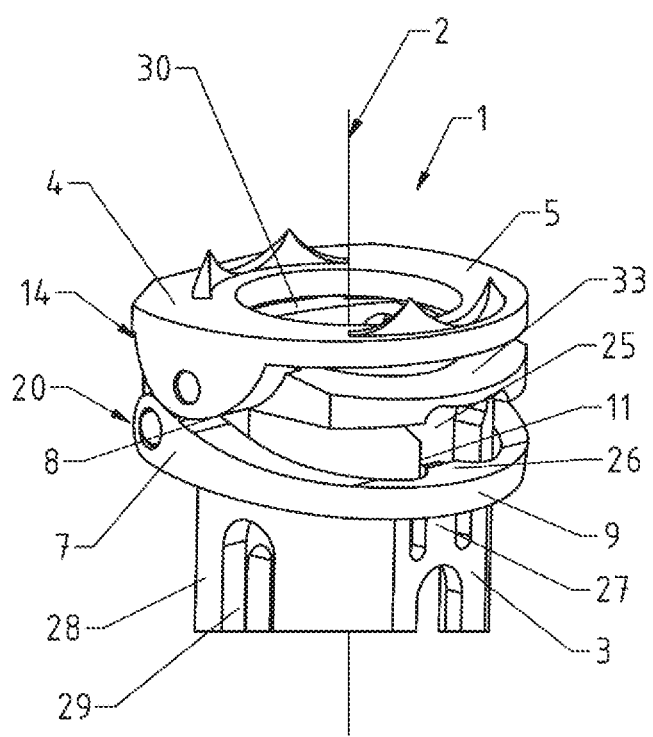
FIG. 1 shows a perspective illustration of the implant of the invention in the pivot configuration.

FIG. 1 shows a perspective illustration of implant 1 of the invention, with a main body 3 which is formed along a longitudinal axis 2 and at one end of which an attachment plate 4 with a contact surface 5 for attachment to an adjacent vertebral body is disposed. Main body 3 is formed as a hollow body with a plurality of recesses 29, formed radially in the circumferential direction on lateral surface 28, for reducing the weight or for providing entries for bone material.

In FIGS. 1 to 6, main body 3 is shown partially along its longitudinal axis 2. Attachment plate 4 on its contact surface 5 has sharp spikes 34 as dislocation protection in regard to the vertebral body. Attachment plate 4 as well has at least one attachment plate recess 30, which in the present case is also formed in the longitudinal direction and is used preferably for the ingrowth of bone material or the introduction of bone cement.

Figure 2:
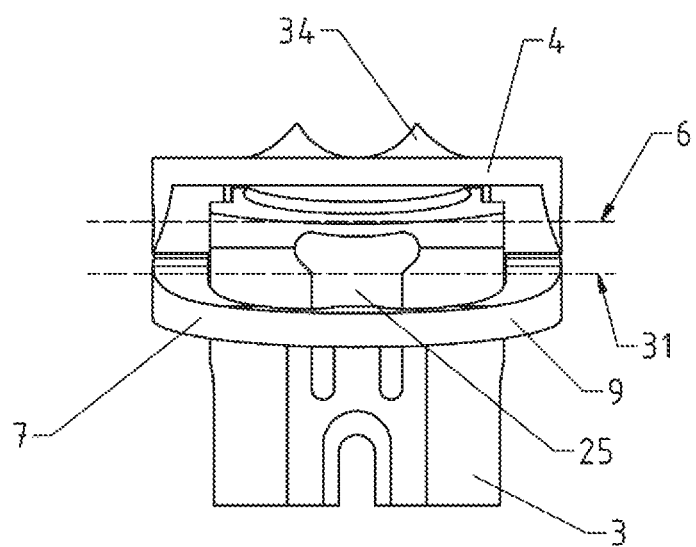
FIG. 2 shows a front view of the implant of the invention in the pivot configuration.
Figure 3:
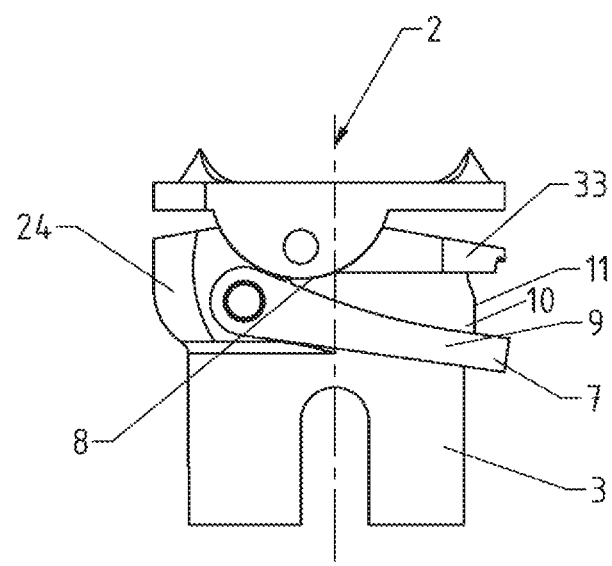
FIG. 3 shows a side view of the implant of the invention in the pivot configuration.
Figure 4:
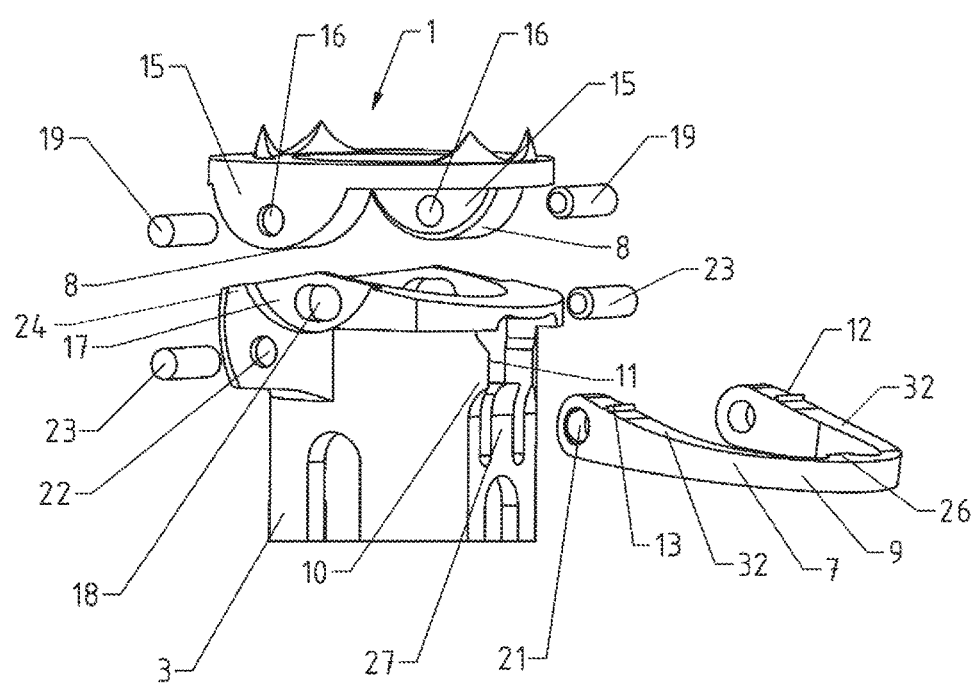
FIG. 4 shows an exploded view of the implant of the invention.
Figure 5:
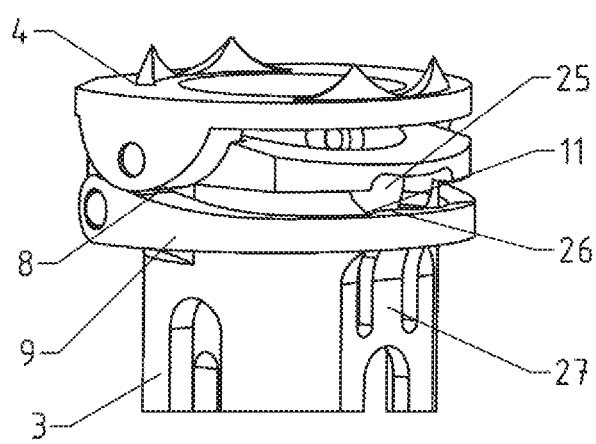
FIG. 5 shows a perspective illustration of the implant of the invention in the clamping configuration.
Figure 6:
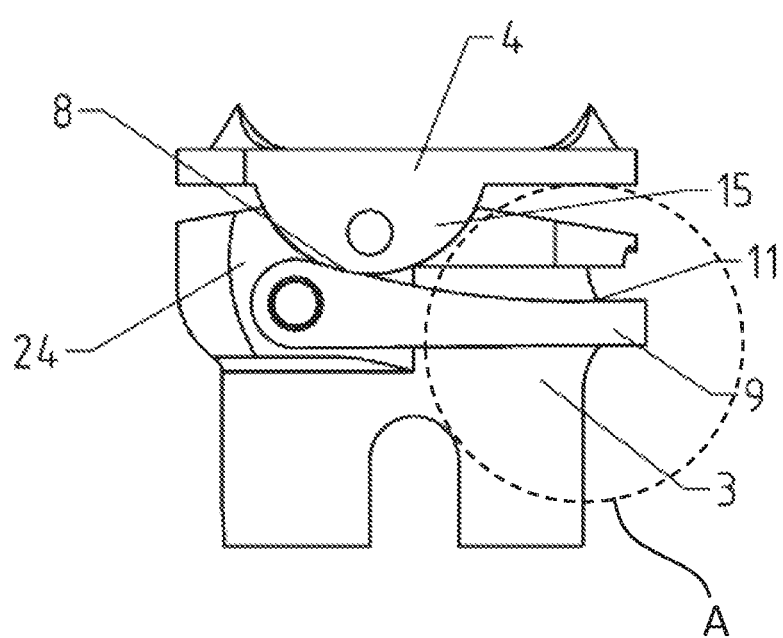
FIG. 6 shows a side view of the implant of the invention in the clamping configuration.

Attachment plate 4 in this case is mounted on main body 3, pivotably about a pivot axis 6 arranged substantially perpendicular to longitudinal axis 2, and can be fixed at an angle relative to this axis or to longitudinal axis 2 (cf. FIG. 2).

The pivotable mounting of attachment plate 4 on main body 3 (cf. FIG. 4) occurs in this case by a pivot unit 14, which comprises a pronounced projection 15 facing main body 3 and on attachment plate 4, with a connecting member seat 16, a projection seat 17, formed in main body 3, with a connecting member opening 18, and a connecting member 19 that can be inserted in connecting member seat 16 and in connecting member opening 18. The individual components of pivot unit 14 can be seen more precisely in FIG. 4. Projection 15 in the present case is formed substantially convex, whereas projection seat 17 is formed as a substantially matching concave area. Projection seat 17 is formed in the shape of a shoulder which is formed on main body 3 and receives or supports projection 15.

Connecting member opening 18 in the present case is shaped as a long hole, especially pronounced radially relative to longitudinal axis 2. Connecting member 19, in contrast, is formed as a pin that is round in cross section, whereby a bolt that is not round in cross section may also be used as connecting member 19. The pin or connecting member 19 is used for fixing attachment plate 4 on main body 3. In other words, therefore, the pin is designed primarily so as to connect attachment plate 4 to main body 3 and to prevent a lifting of attachment plate 4 away from main body 3. Secondarily the maximum pivot angle is limited in the present invention.

Attachment plate 4 in the present case is assigned a plurality, in particular precisely two pivot units 14 distributed uniformly over the circumference. Pivot units 14 in this case can be pivoted about a common pivot axis 6. Moreover, in the present case attachment plate 4 on its side facing main body 3 has precisely two clamping surfaces 8, distributed especially uniformly over the circumference. These are formed on the side, facing main body 3, of the two projections 15.

In order to now be able to fix the angle between attachment plate 4 relative to longitudinal axis 2 or relative to main body 3, a clamping element 7 is provided, which is mounted on main body 3 pivotably about a clamping axis 31 oriented substantially perpendicular to longitudinal axis 2. Clamping element 7 in the present case is formed as a clamping bracket 9, which surrounds at least partially main body 3 circumferentially.

Clamping bracket 9 has a plurality, in the present case precisely two clamping bracket legs 32, and is mounted, movable between two configurations, on main body 3. Clamping bracket 9 is movable between a pivot configuration, in which attachment plate 4 is pivotable, and a clamping configuration, in which the angle and therefore attachment plate 4 can be fixed by an interaction of clamping element 7 with clamping surfaces 8.

Clamping element 7 or clamping bracket 9 in this case is mounted pivotably on main body 3 by a pivot 20, whereby pivot 20 comprises a clamping element connecting member seat 21 formed in clamping element 7, a clamping element connecting member opening 22 formed on main body 3, and a clamping element connecting member 23 inserted in clamping element connecting member seat 21 and in clamping element connecting member opening 22.

Clamping bracket 9 has a plurality, in the present case precisely two pivot 20, whereby in order to increase the stability, clamping bracket 9 has a reinforcement in the area of pivot 20. Moreover, clamping bracket 9 on each clamping bracket leg 32 has a coupling member 12, which is formed as a barb 13 and which in an embodiment of the invention can cut into clamping surface 8 on projection 15. In other words, clamping bracket 9 in the clamping configuration forms a fixed connection with clamping surface 8 of attachment plate 3. Said fixed connection can be a frictional connection, a positive-locking connection, or also a material connection (e.g., adhesive seal).

Furthermore, clamping bracket 9 has a clamping bracket extension 26, which can be taken up in clamping bracket seat 25 formed on main body 3. A flexible element 27 is again formed in addition in the shape of a snap-in element in clamping bracket seat 25; the flexible element has a radially outwardly projecting end and in the pivot configuration is preferably subject to radial pretensioning.

Figure 7A:
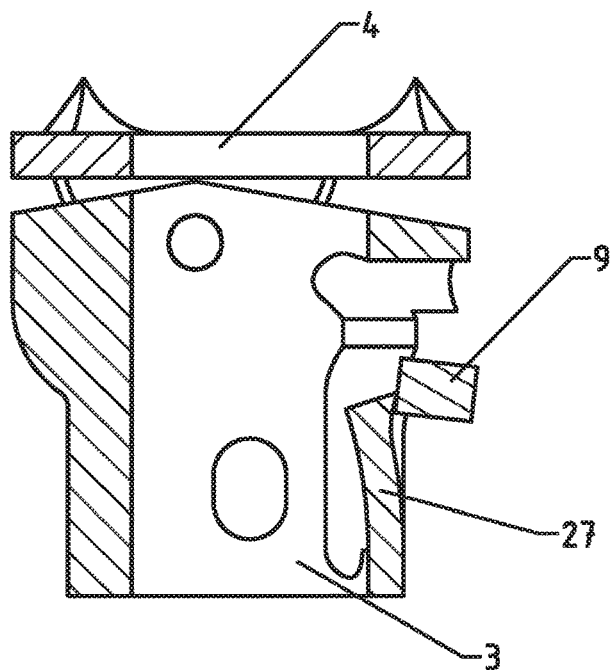
FIG. 7*a* shows a longitudinal section with the detail A from FIG. 6 in the pivot configuration.
Figure 7B:
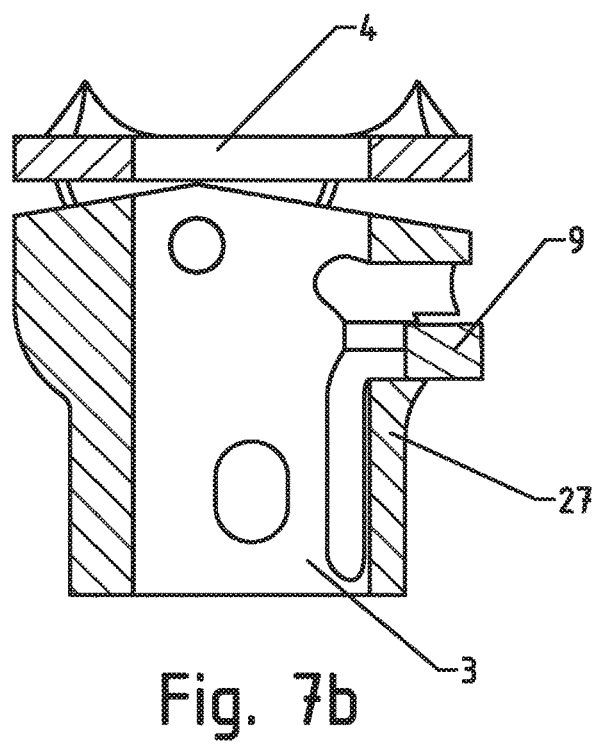
FIG. 7*b* shows a longitudinal section with the detail A from FIG. 6 in the clamping configuration.

This will be evident in greater detail in FIGS. 7a and 7b, which show a detail, namely, area A of the implant. FIG. 7a shows the detail in the pivot configuration and FIG. 7b shows the detail in the clamping configuration. As long as clamping bracket 9 is in the pivot configuration, flexible element 27 lies against it pretensioned within clamping bracket 9. If clamping bracket 9 is pivoted about clamping axis 31 in the direction of attachment plate 4, then flexible element 27 because of the radially acting reset force moves outward and then supports clamping bracket 9 on its side facing away from attachment plate 4. In other words, in the pivot configuration clamping bracket extension 26 lies on the radially outwardly projecting end of flexible element 27, so that flexible element 27 secures clamping bracket 9 in the clamping configuration. There is a positive-locking connection, which is responsible for the clamping of clamping bracket 9 and attachment plate 4.

An alternative embodiment provides that element 27 is made without spring pretensioning, which is then movable manually radially outward or inward, i.e., between the secured and released position, in order to again secure or release the clamping bracket in the clamping configuration.

Furthermore, an extension 10, (cf. FIG. 3) which comprises a planar securing surface 11, is formed on the outer circumference of main body 3. The planar securing surface 11 in this case is oriented parallel to longitudinal axis 2 and is used for the additional securing of clamping bracket 9 in the clamping configuration, in that clamping bracket 9 is pushed over extension 10 and thus forms a fixed connection, preferably a frictional connection with extension 10.

In the present embodiment, main body 3 has a plurality, in particular two planar securing surfaces 11, which are formed circumferentially in the connection to clamping bracket seat 25. Main body 3 furthermore has circumferentially, mainly in the area of pivot unit 14, a reinforcement 24 in which projection seat 17 with connecting member opening 18 and clamping element connecting member opening 22 are formed. Said reinforcement 24 enables a robust structure and prevents the breaking of attachment plate 4 out of main body 3. There is again a saving of material by the selective formation of reinforcement 24 only on pivot unit 14. Furthermore, reinforcement 24 is also formed circumferentially in the shape of an edge 33, which in addition limits the angular position of attachment plate 4 relative to main body 3.

The insertion and fitting of implant 1 of the invention between two vertebral bodies will be described hereafter: After implant 1 is inserted between two vertebral bodies of the spinal column with the use of an instrument (not shown in greater detail), attachment plate 4, which is mounted pivotably on main body 3 and is in contact with the vertebral body via contact surface 5, is adjusted by an angle so that contact surface 5 is oriented optimally relative to the vertebral body. As a result, a stable and comfortable intervertebral connection can be produced. The adjustment of attachment plate 4 in this case requires no additional tightening of screws or other fixing device. Attachment plate 3 can be tilted at an angle about pivot axis 6 by means of pivot unit 14. If the optimal angle is found, clamping bracket 9 is pivoted in the direction of attachment plate 4, as a result of which barbs 13, formed on clamping bracket 9, cut into clamping surface 8 on projection 15 and therefore form a positive-locking connection with clamping surface 8. In addition, however, clamping surface 8, facing main body 3, works together with clamping bracket 9, mounted pivotably on main body 3, and forms a clamping connection, in particular a frictional connection. Clamping element 9 therefore has a counter clamping surface, which faces attachment plate 4 and acts upon clamping surface 8 of attachment plate 4 in the clamping configuration. Clamping bracket 9 is secured by flexible element 27 and/or by a frictional connection (or also by a non-positive connection) between planar securing surfaces 11, formed on the outer side of main body 3, in its clamping configuration.

The securing of the clamping configuration occurs according to an exemplary embodiment of the invention as follows by up to four mechanisms:

the preferably axial securing of clamping bracket 9 in the clamping configuration by the preferably radially movable flexible element 27, alternatively or in addition, by a frictional connection between clamping bracket 9 and clamping surface 8, alternatively or in addition, by a positive-locking connection between barbs 13 and clamping surfaces 8, and alternatively or in addition, by a frictional connection between clamping bracket 9 and securing surfaces 11.

In the case of a reversible clamping configuration, the set and fixed angle can be corrected or optimized again subsequently by moving or pivoting clamping bracket 9 again in the direction of main body 3 and therefore loosening the clamping connection between clamping bracket 9 and clamping surface 8. In addition, the positive-locking connection between barbs 13 and clamping surfaces 8 and the frictional connection between clamping bracket 9 and securing surfaces 11 have to be loosened, as a result of which clamping bracket 9 is then moved again in the pivot configuration. Attachment plate 4 can now be pivoted anew about pivot axis 6 and the angle between attachment plate 4 and main body 3 can be reoriented.

Attachment plate 4 and thereby the angle can be fixed again back into the clamping configuration by the above-described movement of clamping bracket 9. In the case of an irreversible clamping configuration, two predetermined breaking points are formed in the material on clamping bracket 9 (for example, notches or weak spots), so that parts of clamping bracket 9 can be broken off if it has assumed the clamping configuration. Clamping bracket 9 can also have both a reversible and irreversible clamping configuration; i.e., clamping bracket 9 can be moved reversibly between the clamping configuration and the pivot configuration until clamping bracket 9 is broken off and then assumes an irreversible clamping configuration.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An implant for insertion between vertebral bodies of the spinal column, the implant comprising:
   a main body that is formed along a longitudinal axis;
   an attachment plate, with a contact surface for attachment to an adjacent vertebral body, arranged on at least one end of the main body, the attachment plate being pivotably mounted on the main body about a pivot axis and arranged substantially perpendicular to the longitudinal axis, the attachment plate being adapted to be fixed at an angle relative to the longitudinal axis; and
   at least one clamping element assigned to the main body, wherein the attachment plate has a clamping surface on a side facing the main body, and
   wherein the clamping element is movable between a pivot configuration, in which the attachment plate is pivotable, and a clamping configuration, in which the angle and thereby the attachment plate are fixed by an interaction of the clamping element with the clamping surface.

2. The implant according to claim 1, wherein the clamping element is mounted on the main body pivotably about an axis arranged substantially perpendicular to the longitudinal axis.

3. The implant according to claim 2, wherein the attachment plate and the main body are connected to one another by a pivot unit, which comprises a projection facing the main body, with a connecting member seat and a projection seat formed on the main body, with a connecting member opening and a connecting member inserted in the connecting member seat and in the connecting member opening.

4. The implant according to claim 3, wherein the projection is formed at least partially convex and wherein the projection seat is formed at least partially concave.

5. The implant according to claim 3, wherein the clamping element and the main body are connected to one another by a pivot, which comprises a clamping element connecting member seat formed on the clamping element, a clamping element connecting member opening formed on the main body, and a clamping element connecting member inserted in the clamping element connecting member seat and in the clamping element connecting member opening.

6. The implant according to claim 5, wherein the main body at an end facing the pivot has a reinforcement, in which the projection seat with the connecting member opening and the clamping element connecting member opening are formed.

7. The implant according to claim 1, wherein the clamping element is formed as a clamping bracket that surrounds at least partially the main body circumferentially.

8. The implant according to claim 7, wherein the main body has a clamping bracket seat for receiving a clamping bracket extension formed on the clamping bracket.

9. The implant according to claim 8, wherein a flexible element is disposed on the main body for securing the clamping element in the clamping configuration.

10. The implant according to claim 9, wherein the flexible element is pretensioned radially in the pivot configuration.

11. The implant according to claim 9, wherein the flexible element in the pivot configuration acts axially on the clamping bracket extension and wherein the clamping bracket extension in the clamping configuration acts radially together with the clamping bracket seat.

12. The implant according to claim 1, wherein an extension, which comprises an at least partially planar securing surface, is formed or disposed on an outer circumference of the main body.

13. The implant according to claim 12, wherein the extension is inclined at a tilt angle or is oriented substantially parallel to the longitudinal axis.

14. The implant according to claim 1, wherein the clamping element is assigned at least one coupling member on a side facing the clamping surface for additional securing of the clamping configuration.

15. The implant according to claim 14, wherein the coupling member is formed as a single barb or as a plurality of barbs.

16. The implant according to claim 1, wherein the attachment plate and the main body are connected to one another by a pivot unit, which comprises a projection facing the main body, with a connecting member seat and a projection seat formed on the main body, with a connecting member opening and a connecting member inserted in the connecting member seat and in the connecting member opening.

17. The implant according to claim 1, wherein a flexible element is disposed on the main body for securing the clamping element in the clamping configuration.

18. An implant for insertion between vertebral bodies of the spinal column, the implant comprising:
    a main body that is formed along a longitudinal axis;
    an attachment plate, with a contact surface for attachment to an adjacent vertebral body, arranged on the main body, the attachment plate being pivotably mounted on the main body about a pivot axis and arranged substantially perpendicular to the longitudinal axis, the attachment plate being adapted to be fixed at an angle relative to the longitudinal axis; and
    a pivoting clamping bracket assigned to the main body, wherein the attachment plate has a clamping surface on a side facing the main body, and
    wherein the pivoting clamping bracket is movable between a pivot configuration, in which the attachment plate is pivotable, and a clamping configuration, in which the angle and thereby the attachment plate are fixed by an interaction of the pivoting clamping bracket with the clamping surface.

19. The implant according to claim 18, further comprising a barb on a side facing the clamping surface for additional securing of the clamping configuration.

20. The implant according to claim 18, wherein the attachment plate and the main body are connected to one another by a pivot unit, which comprises:
    a seat with an opening; and
    a pin inserted in the seat and in the opening.

* * * * *